United States Patent [19]

Jori et al.

[11] Patent Number: 5,015,478

[45] Date of Patent: May 14, 1991

[54] PORPHYCENE ANTI-CANCER AGENTS AND TREATMENT METHODS

[75] Inventors: Giulio Jori, Padova, Italy; Matthias Köcher, Overath; Emanuel Vogel, Cologne, both of Fed. Rep. of Germany; Alexander D. Cross, Atherton, Calif.

[73] Assignee: Cytopharm, Inc., Menlo Park, Calif.

[21] Appl. No.: 432,701

[22] Filed: Nov. 22, 1989

Related U.S. Application Data

[62] Division of Ser. No. 232,411, Aug. 15, 1988, Pat. No. 4,913,907.

[51] Int. Cl.$^5$ ............................................. A61K 37/22
[52] U.S. Cl. ..................................... 424/450; 424/1.1; 514/410; 604/49
[58] Field of Search ................. 424/450, 1.1; 514/410; 604/49

[56] References Cited

U.S. PATENT DOCUMENTS

| | | | |
|---|---|---|---|
| 4,448,765 | 5/1984 | Ash | 424/74 |
| 4,452,747 | 6/1984 | Gersonde | 264/41 |
| 4,649,151 | 3/1987 | Dougherty | 514/410 |
| 4,656,186 | 4/1987 | Bommer et al. | 514/410 |
| 4,693,885 | 9/1987 | Bommer et al. | 514/410 |

*Primary Examiner*—Merrell C. Cashion, Jr.
*Assistant Examiner*—P. L. Prater
*Attorney, Agent, or Firm*—William B. Walker

[57] ABSTRACT

The therapeutic compositions of this invention comprise one or more porphycene compounds incorporated within liposomes. The method of this invention for treating cancer comprises administering a therapeutically effective amount of a porphycene derivative to a patient, and exposing an affected body area of the patient to a therapeutically sufficient amount of light having a wavelength of from 600 to 950 nm.

9 Claims, No Drawings

PORPHYCENE ANTI-CANCER AGENTS AND TREATMENT METHODS

This application is a division of application Ser. No. 07/232,411 filed on Aug. 15, 1988, now U.S. Pat. No. 4,913,907.

FIELD OF THE INVENTION

This invention relates to novel compositions including one or more porphycene compounds, and the use thereof for therapeutic treatment.

BACKGROUND OF THE INVENTION

Enormous financial, medical and scientific efforts have been applied during the past fifty years to address the health problems presented by cancer, a leader killing disease on a global scale. Partial successes have been recorded for treatments employing radiation, surgical procedures, and chemotherapy. However, many difficulties remain. Side effects of both radiation and chemotherapy treatments are frequently severe, and can threaten or terminate a patient's life. Destruction of bone marrow with consequent reduction of blood cell populations lowers the patient's resistance to bacterial and viral infection, and exposes the patient to high risk of opportunistic infection. Chemotherapeutic agents are generally highly toxic substances. Early trials of cytokines, while offering promise, have also shown unexpected side effects. Adjunct therapies, with cell stimulating factors compensating for diminished cell production from reduced bone marrow, and combination therapies (e.g., Interleukin-2 and interferons) are being investigated.

A major improvement in cancer therapy would be provided by an agent which is innocuous or largely nontoxic of itself, but which is capable of generating a lethal entity when appropriately activated or triggered. Activation should be specific and occur only after the agent has concentrated in or bound to the target cancer cell. The sites of cancerous tissues can be generally located prior to therapy using standard techniques with radiolabeled antibodies and/or nuclear imaging scanning procedures.

DESCRIPTION OF THE PRIOR ART

Vogel et al, *Angew. Chem.* 98:262 (1986) describe the synthesis of porphycene. Synthesis of methyl, ethyl and propyl 2,7,12,17-substituted porphycenes were reported by Vogel et al, *Angew. Chem.* 99:909–917 (1987). The photophysical properties of porphycene and 2,7,12,17-tetra-n-propylporphycene are described by Aramendia et al, *Photochem. Photobiol.* 44:555–559 (1986). They are shown to possess a high level of stability towards photooxidation, high absorption above 620 nm, and high quantum yields of fluorescence and singlet oxygen sensitization. The photoexcited triplet states of porphycene, 2,7,12,17-tetra-n-propylporphycene and 9,10,19,20-tetra-n-propylporphycene have been studied by jointly by the groups of Levanon and Vogel, as reported in Ofir et al, *J. Phys. Chem.* 39:2686–2688 (1987). Porphycenes are not soluble in water, and no method for administration of porphycenes to living organisms has been shown.

In vitro photochemical studies indicate that highly active singlet molecular oxygen (SMO, or singlet oxygen) is produced by irradiation of certain porphyrins, such as hematoporphyrins. Porphyrins have been shown in vivo to concentrate in cancerous tumors. U.S. Pat. No. 4,649,151 discloses novel porphyrins and treatment of cancerous tumors with the porphyrins. However, because the porphyrins also bind to other, noncancerous cells, some healthy cell destruction also occurs. Some porphyrins are soluble in water, and may be administered by intravenous injection. A relatively large dosage of porphyrins must be administered, as the porphyrins absorb light energy poorly above 600 nm. At shorter wavelengths porphyrins absorb more strongly, but the absorption overlaps with the very intense absorption of the red blood cells. In clinical use, general skin photosensitivity has been observed weeks after administration of the porphyrins as a consequence of the slow clearance of porphyrins from cutaneous tissues.

Multilamellar liposomes, or microvesicles, are onion-like structures having a series of lipid layers spaced from one another by aqueous material, with the outermost layer being lipid. Unilamellar bodies, a single lipid bilayer enclosing an aqueous compartment, are also known. Liposomes are described in U.S. Pat. Nos. 4,452,747 and 4,448,765. Liposomes including porphyrin are described in Jori et al, *Brit. J. Canc.* 56:597–600 (1983).

SUMMARY OF THE INVENTION

The therapeutic compositions of this invention comprise one or more porphycene compounds incorporated within a liposome. The method of this invention for treating cancer comprises administering a therapeutically effective amount of one or more porphycene compounds incorporated into liposomes to a patient having cancer, and exposing the patient's affected body area, which has accumulated the porphycene, to a therapeutically sufficient amount of light having a wavelength of from 600 to 950 nm, preferably from 600 to 750 nm.

The porphycene compounds are represented by Formula I and Formula II:

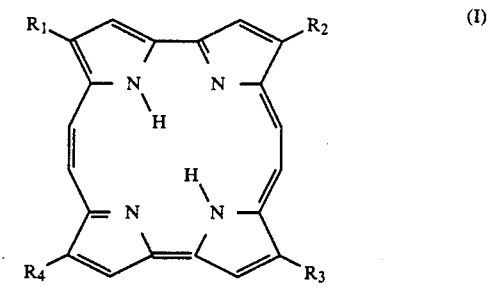

In the compounds of Formula I, $R_1$, $R_2$, $R_3$, and $R_4$ are hydrogen or a lower alkyl having from 1 to 6 carbons.

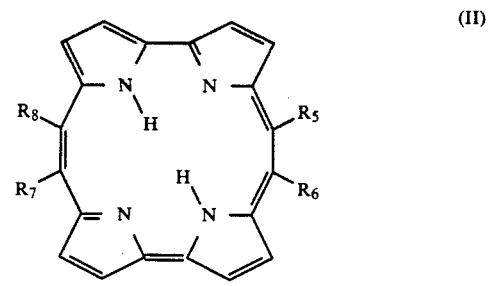

In the compounds of Formula II, $R_5$, $R_6$, $R_7$, and $R_8$ are hydrogen or a lower alkyl having from 1 to 6 carbons.

DETAILED DESCRIPTION

Porphycene is a tetrapyrrole molecule activated by light in the 600–950 nm range. Irradiation with activating light leads to the production of highly energized photochemical radicals. Based on in vitro studies, the production of singlet molecular oxygen is probable. However, this has not been yet completely established by in vivo studies. The term "singlet molecular oxygen" and "SMO", as used herein, are thus defined as meaning these highly energized photochemical radical products of in vivo photoactivation of porphycenes, including but not limited to singlet molecular oxygen radicals.

Singlet molecular oxygen causes cell destruction and necrosis in nearby tissues. However, porphycene and alkylated porphycenes are not soluble in water and pharmaceutically suitable solvents. They are thus not amenable to injection in aqueous media. Porphycene compounds, including porphycene and tetra-alkyl substituted porphycenes of Formulas I and II are useful in the methods and compositions of this invention.

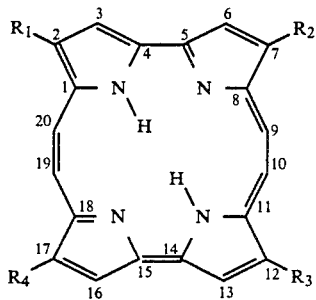

(I)

In the compounds of Formula I, $R_1$, $R_2$, $R_3$, and $R_4$ are hydrogen or a lower alkyl having from 1 to 6 carbons.

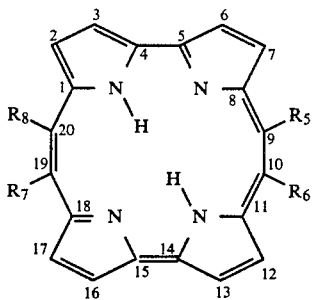

(II)

In the compounds of Formula II, $R_5$, $R_6$, $R_7$, and $R_8$ are hydrogen or a lower alkyl having from 1 to 6 carbons.

The term "alkyl" as used herein includes both straight and branch-chained saturated aliphatic groups.

The compounds of Formula I and II can be prepared by reductive coupling corresponding lower alkyl substituted 5,5'-diformyl-2,2'-bipyrroles or coupling 5,5'-di-(lower alkyl)-carbonyl-2,2'-bipyrroles according to procedures described by Vogel et al., *Angew. Chem.* 99:909–917 (1987).

Porphycenes are related to the porphyrins. However, porphycenes have several advantages as compared to the porphyrins which make them particularly suitable as phototherapeutic agents. Due to the chemical structure of porphycenes they are more efficient generators of SMO than the porphyrins, producing SMO faster and in greater quantity than comparable porphyrins. Each porphycene molecule can produce multiple SMO moieties upon irradiation.

The penetration of the therapeutically important red light having a frequency above 600 nm through tissue is limited by melanine absorption and light scattering. This filter and shielding effect decreases with increasing wavelength. Since porphycenes absorb more strongly than the porphyrins in the higher-than-600 nm region, lower doses of porphycenes and/or lower dosages of light are thus required for porphycene treatment than are necessary with porphyrin treatment, to achieve a given phototherapeutic result.

LIPOSOMES

Liposomes are onion-like structures having a series of lipid layers spaced from one another by aqueous material, with the outermost layer being lipid. Unilamellar bodies, a single lipid bilayer enclosing an aqueous compartment, are also known, and are described in U.S. Pat. Nos. 4,452,747 and 4,448,765, which are incorporated herein by reference in their entireties. In the lipid vesicles, the substance dissolved in the solvent is enclosed by phospholipid bilayer membrane. The lipid membrane has a thickness of typically 3 to 5 nm, and the vesicles have a diameter from 15 to 120 nm. The size of the vesicles can be determined by laser light scattering, ultracentrifugation, gel-filtration or electron scanning microscopy.

Unlike porphyrins, porphycenes are generally insoluble in water and polar solvents. Although emulsions or solutions of porphycenes for injection can be made, they are less physiologically compatible, and therefore less desirable than incorporation of the porphycene within liposomes. In accordance with the invention herein, porphycenes can be made physiologically compatible by incorporation into liposomes. Porphycene compound-containing liposomes are administered into a patient having cancer. Radiation is then used to selectively activate the porphycene compound, resulting in necrosis and death of the cancerous tissue.

In a mouse model, tetra-n-propylporphycene was seen to concentrate preferentially in tumor tissue as compared to skin or muscle tissue at 24 hours post-injection. There was little or no porphycene uptake by the brain. Drug clearance was via the liver rather than by the kidneys.

THERAPEUTIC METHODS

The phototherapeutic approach to cancer treatment herein involves binding or concentrating one or more porphycene compound in tumor tissue. Porphycene compounds are substantially less toxic or hazardous in their unexcited state than cytotoxins incorporating ribosomal inhibiting proteins. This physiologically tolerated substance is then exposed to activating radiation with a low likelihood of hazard.

This novel therapeutic approach has a variety of advantages. The chemical agent, a porphycene, is minimally toxic in the unexcited state. Each porphycene molecule can be repeatedly photoactivated and lead each time to cell-lethal events. The source of the cell-lethal agent is endogenous within the patient. SMO is likely to play a major role in the cell-lethal events. The half-life of the SMO toxin is approximately $4\mu$ seconds in water at room temperature, allowing contact with the target cell while providing minimal migration in the lethal form to neighboring healthy tissue cells. Preferably, the singlet oxygen molecules rupture chemical bonds in the target cell wall, which results in the destruction of the target cell. Lethal attack commences promptly upon irradiation in the immediate vicinity of the singlet oxygen producer, which disrupts the cell wall and destroys the integrity of the target cell. Unreacted SMO decays rapidly to ground state oxygen, giving oxygen molecules as its primary decay product.

The therapist (e.g., physician or radiologist) can select the time and duration of therapy, repeating the irradiation treatment at intervals, with the same agent molecules bound to the target cell. Booster doses of the singlet oxygen producer may be given.

The dosage of the cytotoxic agent may be varied according to the size and location of the target tissues which are to be destroyed, and the method of administration. Generally, the dosage will be in the range of 0.5 to 20.0 milligrams of porphycene compound per kilogram of body weight, more preferably in the range of 0.5 to 5.0 milligrams per kilogram. The liposomes incorporating one or more porphycenes may be administered intravenously, intraarterially, or directly proximal to the tumor.

Irradiation will generally take place not less than 1 hour nor more than 4 days after introduction of the cytotoxic agent. More usually, phototherapy will be administered from 3 hours to 48 hours after administration of the cytotoxic agent. Exposure to non-therapeutic light sources should be avoided immediately following phototherapy, to minimize light toxicity.

A variety of phototherapy and irradiation methodologies are well known to those skilled in the art, and may be used in conjunction with the novel compounds herein. For example, at beginning at about 620 nm, radiation can penetrate human tissue to a depth of up to about 2 cm. Unfocused light may be administered to a patient topically. Appropriate draping can be used to limit the penetration area of the light if desired.

Light sources which are appropriate for such use are well known to the art, and may vary from white light sources with appropriate filters, to lasers. Preferred wavelengths are from 600 to 950 nm, more preferably 700 to 950 nm. The total amount of light which is applied to a tumor will vary with the methods used and the location of the tumor, but will generally be in the range of 50 to 1,000 J/cm$^2$, more usually in the range of 100 to 350 J/cm$^2$.

In a preferred embodiment, focused radiation is administered internally in a patient, using flexible fiberoptic catheters or other endoscopic devices to deliver the necessary radiation to the site of the bound porphycenes. Fiberoptic catheters are available commercially.

This invention is further illustrated by the following specific but non-limiting examples. Temperatures are given in degrees Centigrade and percentages as weight percents unless otherwise specified. Procedures which have been previously carried out are presented in the past tense, and procedures which are being constructively reduced to practice in this application are presented in the present tense.

EXAMPLE 1

Synthesis of 2,7,12,17-tetra-n-substituted Porphycenes 2,7,12,17-tetra-n-propylporphycene (TPP) (Formula I) is produced by the methods of E. Vogel et al, *Angew.-Chem.* 99:909–912 (1987).

Repeating the procedure, but replacing the 5,5'-diformyl-4,4'-di-n-propyl-2,2'-bipyrrole with 5,5'-diformyl-2,2'-bipyrrole; 5,5'-diformyl-4,4'-dimethyl-2,2'-bipyrrole; 4,4'-diethyl-5,5'-diformyl-2,2'-bipyrrole; 4,4'-di-n-butyl-5,5'-diformyl-2,2'-bipyrrole; 5,5'-diformyl-4,4'-di-n-pentyl-2,2'-bipyrrole; and 5,5'-diformyl-4,4'-di-n-hexyl-2,2'-bipyrrole, yields the corresponding porphycene; 2,7,12,17-tetramethylporphycene; 2,7,12,17-tetraethylporphycene; 2,7,12,17-tetra-n-butylporphycene; 2,7,12,17-tetra-n-pentylporphycene; and 2,7,12,17-tetra-n-hexylporphycene.

EXAMPLE 2

Preparation of Liposomes 1.5 mg of 2,7,12,17-tetra-n-propylporphycene (TPP) (E. Vogel et al, *Angew.Chem.* 99:909–912 (1987)) and 80 mg dipalmitoyl-phosphatidylcholine (DPPC) (crystalline DL-α-DPPC, Sigma) were dissolved in a binary mixture of CHCl$_3$:CH$_3$OH (9:1, v/v). After gentle magnetic stirring for approximately 10 minutes, the solvent was removed by rotary evaporation under reduced pressure. The film was resuspended in 5 mL of phosphate-buffered saline (PBS, pH 7.4) with vigorous stirring, and then sonicated at 55° C. for 30 minutes. The dispersion thus obtained was allowed to cool to 25° C., and was centrifuged for 5 minutes at 3,000 rpm. A small aliquot of the supernatant was assayed for endoliposomal TPP content. The liposomes appeared to have an average external radius of approximately 26 nm by electron microscopy.

EXAMPLE 3

Liposomes Incorporating Porphycene Derivatives

Repeating the procedures of Example 2 but replacing the tetra-n-propylporphycene with one or more products of Example 1 yields liposomes incorporating porphycene; 2,7,12,17-tetramethylporphycene; 2,7,12,17-tetraethylporphycene; 2,7,12,17-tetra-n-butylporphycene; 2,7,12,17-tetra-n-pentylporphycene; 2,7,12,17-tetra-n-hexylporphycene; and mixtures thereof.

EXAMPLE 4

Phototherapy

Female Balb/c mice had a MS-2 fibrosarcoma transplanted in the right hind leg. By the seventh day after transplantation, the tumors had reached a diameter of approximately 0.8 cm.

Each mouse was intravenously injected with 2 mg./kg. of 2,7,12,17-tetra-n-propylporphycene (TPP) incorporated into small unilamellar liposomes of dipalmitoyl-phosphatidylcholine (DPPC), prepared according to the procedures of Example 2, on the seventh day after transplantation. At this time the diameter of the tumor was approximately 0.8 cm.

24 hours after TPP injection, the tumor area was exposed to 600–690 nm. light isolated by optical filtration from the emission of a 250 W quartz-halogen lamp through a set of optical filters (Teclas, Lugano, Switzerland). The light beam was focused into a bundle of optical fibers having an external diameter of 6 mm. The tip of the fiber was kept at a distance of 1 cm from the tissue surface. The lamp was operated at a dose-rate of 230 mW/cm², and the total delivered light dose was 150 J/cm² or 300 J/cm².

An equal area of normal skin on the left hind leg was irradiated in each mouse immediately after tumor irradiation using an identical protocol.

Irradiation of TPP-untreated mice under the experimental conditions caused no detectable damage to the tumor area or to normal skin.

Irradiation of the mice with 300 J/cm² at 24 hours after TPP injection caused the onset of massive tumor necrosis, with eschar formation complete within 3 days. The depth of necrosis continued until bone was reached, at about 7 days. An equally deep necrosis, however less extensive, was obtained upon administration of 150 J/cm² of red light. Most irradiated TPP-treated mice developed some photoinduced damage at the level of the normal skin. Such damage mainly consisted of erythema, the extent of which was generally limited (diameter less than 0.3 cm) and which disappeared within about one week. Some photosensitivity was also observed at the irradiated normal skin of the left hind leg.

EXAMPLE 5

Tissue analysis, Tetra-n-propylporphycene

At each of 3 hours and 24 hours after injection, six mice were sacrificed by exposure to ether vapor, and the serum or specific tissues were removed. About 2 mL of blood was taken intracardially and centrifuged for 15 minutes at 3,000 rpm to remove the erythrocytes. The serum was collected, diluted with 2% aqueous SDS and assayed for TPP content spectrophotofluorimetrically ($\lambda_{ex}$=560 nm). The fluorescence emitted in the 580–740 nm interval was converted into TPP concentration by interpolation with a calibration plot.

The tumor and predetermined normal tissues were removed, washed twice with PBS, and a weighed amount of tissue (approximately 200 mg) was finely minced and homogenized in a Potter vessel with 4 mL chloroform. The dispersion was centrifuged at 3,000 rpm for 15 minutes; the supernatant was collected and its TPP content was estimated spectrophotofluorimetrically as described above. Rehomogenization of the sediment under the same conditions gave less than 3% of the TPP extracted in the original step.

A serum sample (0.75 mL) was added with an equal volume of PBS and then eluted at room temperature through a column (1.7×140 cm) of Sephacryl S-300 which had been previously equilibrated with pH 7.4 Na₂HPO₄-KH₂PO₄ buffer at ionic strength 0.1, according to the procedures of Reddi et al, Brit.J.Canc. 56:507–600 (1987), the disclosure of which are incorporated herein by reference.

The recovery of TPP from serum and various tissues of the tumor-bearing mice at 3 hours and 24 hours after injection are shown in Table 1. The samples from each animal were analyzed separately, and the table values represent the average recovery data from the single tissues of 6 mice. The maximum deviation from the reported values was ±20%. No TPP-type fluorescence was observed in the tumor and healthy tissues obtained from mice not injected with TPP.

The recovery from the tumor was approximately 1 μg/g (microgram per gram) of tissue. The 24-hour ratios of TPP concentration between tumor and (healthy, peri-tumoral) muscle was approximately 17:1. This indicates that the selective concentration of TPP into tumor cells was good. The ratio of concentration of TPP in the tumor and that in healthy skin was approximately 3:1. This indicates a relatively low risk of general photosensitivity.

TABLE A

| Site | Recovery after 3 hours* | Recovery after 24 hours* |
|---|---|---|
| Serum | 122.53 | 25.56 |
| Liver | 13.03 | 11.09 |
| Skin | 0.29 | 0.44 |
| Muscle | 0.14 | 0.09 |
| Brain | <0.01 | <0.01 |
| Spleen | 6.85 | 2.94 |
| Kidneys | 1.25 | not determined |
| Tumor | 0.69 | 1.50 |

*μg (micrograms) per gram of tissue or per mL of serum

We claim:
1. A method for treating cancer comprising
   (a) administering a therapeutically effective amount of at least one porphycene compound of Formula I or Formula II to a patient; and
   (b) exposing the body area of the patient having the cancer to a therapeutically sufficient amount of light having a wavelength of from 600 to 950 nm;

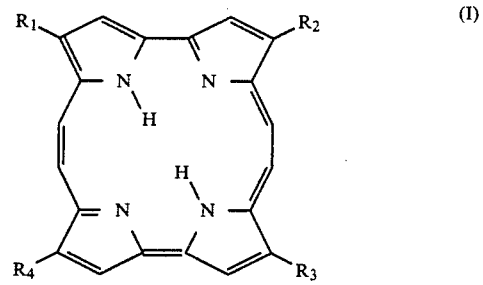

wherein $R_1$, $R_2$, $R_3$, and $R_4$ are hydrogen or a lower alkyl having from 1 to 6 carbons;

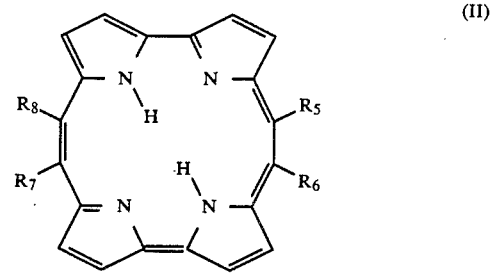

wherein $R_5$, $R_6$, $R_7$, and $R_8$ are hydrogen or a lower alkyl having from 1 to 6 carbons.

2. A method according to claim 1 wherein therapeutically sufficient amount of light has a wavelength of from 600 to 950 nm.

3. A method according to claim 1 including a porphycene compound of Formula I.

4. A method according to claim 3 including a porphycene compound selected from the group consisting of
2,7,12,17-tetramethylporphycene,
2,7,12,17-tetraethylporphycene,
2,7,12,17-tetra-n-propylporphycene,
2,7,12,17-tetra-n-butylporphycene,
2,7,12,17-tetra-n-pentylporphycene, 2,7,12,17-tetra-n-hexylporphycene, and mixtures thereof.

5. A method according to claim 1 wherein the porphycene compound is a porphycene compound of Formula II.

6. A method according to claim 5 including a porphycene compound selected from the group consisting of
9,10,19,20-tetramethylporphycene,
9,10,19,20-tetraethylporphycene,
9,10,19,20-tetra-n-propylporphycene,
9,10,19,20-tetra-n-butylporphycene,
9,10,19,20-tetra-n-pentylporphycene,
9,10,19,20-tetra-n-hexylporphycene, and mixtures thereof.

7. A method according to claim 1 wherein the porphycene compound is porphycene.

8. A method according to claim 1 wherein the porphycene is incorporated into a unilamellar liposome.

9. A method according to claim 1 wherein the porphycene is incorporated into a multilamellar liposome.

* * * * *